United States Patent
Toyama et al.

(10) Patent No.: US 9,441,077 B2
(45) Date of Patent: Sep. 13, 2016

(54) MANUFACTURING METHOD FOR ORGANOPOLYSILOXANE-POLYOXY-ALKYLENE BLOCK COPOLYMER

(71) Applicant: Dow Corning Toray Co., Ltd., Tokyo (JP)

(72) Inventors: Takatoshi Toyama, Chiba (JP); Masaru Ozaki, Ichihara (JP); Seiji Hori, Sabae (JP); Mari Wakita, Chiba (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 0 days.

(21) Appl. No.: 14/365,883

(22) PCT Filed: Dec. 4, 2012

(86) PCT No.: PCT/JP2012/081869
§ 371 (c)(1),
(2) Date: Jun. 16, 2014

(87) PCT Pub. No.: WO2013/089043
PCT Pub. Date: Jun. 20, 2013

(65) Prior Publication Data
US 2014/0336401 A1 Nov. 13, 2014

(30) Foreign Application Priority Data

Dec. 16, 2011 (JP) .............................. JP2011-275720

(51) Int. Cl.
*C08G 77/46* (2006.01)
*A61Q 5/00* (2006.01)
*A61K 8/898* (2006.01)
*A61K 8/894* (2006.01)

(52) U.S. Cl.
CPC .............. *C08G 77/46* (2013.01); *A61K 8/894* (2013.01); *A61K 8/898* (2013.01); *A61Q 5/00* (2013.01); *A61K 2800/594* (2013.01)

(58) Field of Classification Search
CPC ....... C08G 77/46; A61K 8/894; A61K 8/898
See application file for complete search history.

(56) References Cited

U.S. PATENT DOCUMENTS

| | | | |
|---|---|---|---|
| 3,957,842 A | 5/1976 | Prokai et al. | |
| 5,472,686 A * | 12/1995 | Tsubaki et al. | ................. 424/59 |
| 5,767,219 A | 6/1998 | Takarada et al. | |
| 2008/0014166 A1* | 1/2008 | Klug et al. | ................. 424/70.12 |

FOREIGN PATENT DOCUMENTS

| | | |
|---|---|---|
| JP | 04-211605 A | 8/1992 |
| JP | H 04-234307 A | 8/1992 |
| JP | H 05-310944 A | 11/1993 |
| JP | H 09-151119 A | 6/1997 |
| JP | H 09-183854 A | 7/1997 |
| JP | H 09-268230 A | 10/1997 |

OTHER PUBLICATIONS

International Search Report for Application No. PCT/JP2012/081869 dated May 7, 2013, 3 pages.
English language abstract for JPH 04-211605 extracted from the PAJ database on Aug. 20, 2014, 1 page.
English language abstract for JPH 04-234307 extracted from the PAJ database on Aug. 20, 2014, 1 page.
English language abstract and machine-assisted English translation for JPH 05-310944 extracted from the PAJ database on Aug. 20, 2014, 25 pages.
English language abstract and machine-assisted English translation for JPH 09-151119 extracted from the PAJ database on Aug. 20, 2014, 42 pages.
English language abstract and machine-assisted English translation for JPH 09-183854 extracted from the PAJ database on Aug. 20, 2014, 48 pages.
English language abstract for JPH 09-268230 extracted from espacenet.com database on Aug. 20, 2014, 2 pages.

* cited by examiner

*Primary Examiner* — Sudhakar Katakam
(74) *Attorney, Agent, or Firm* — Howard & Howard Attorneys PLLC

(57) ABSTRACT

The present invention relates to a manufacturing method for an organopolysiloxane-polyoxyalkylene block copolymer obtained by condensation reaction of a polyoxyalkylene compound having a particular chemical structure and an organopolysiloxane having a particular chemical structure. The manufacturing method according to the present invention can enable an easy manufacturing of a high molecular weight organopolysiloxane-polyoxyalkylene block copolymer and provide an organopolysiloxane-polyoxyalkylene block copolymer where an amount of volatile cyclic polysiloxane produced as a by-product is small.

9 Claims, No Drawings

MANUFACTURING METHOD FOR ORGANOPOLYSILOXANE-POLYOXYALKYLENE BLOCK COPOLYMER

RELATED APPLICATIONS

This application is the National Stage of International Patent Application No. PCT/JP2012/081869, filed on Dec. 4, 2012, which claims priority to and all the advantages of Japanese Patent Application No. JP2011-275720, filed on Dec. 16, 2011, the content of which is incorporated herein by reference.

TECHNICAL FIELD

The present invention relates to a manufacturing method for an organopolysiloxane-polyoxyalkylene block copolymer where an amount of volatile cyclic polysiloxane produced as a by-product is small, and by which a high molecular weight organopolysiloxane-polyoxyalkylene block copolymer can be obtained.

BACKGROUND ART

Conventional technologies by which an organopolysiloxane-polyoxyalkylene block copolymer is manufactured via an addition reaction of a silicon-bonded hydrogen atom-containing polysiloxane and a silicon-bonded aliphatic unsaturated group-containing polyoxyalkylene are known.

For example, Japanese Unexamined Patent Application Publication Nos. H04-211605, H04-234307, and H09-268230 describe manufacturing an organopolysiloxane-polyoxyalkylene block copolymer via a hydrosilylation reaction of a polysiloxane having silicon-bonded hydrogen atoms on both molecular terminals and a polyoxyalkylene having silicon-bonded aliphatic unsaturated groups on both molecular terminals in the presence of a platinum catalyst.

Additionally, Japanese Unexamined Patent Application Publication Nos. H05-310944, H09-151119, and H09-183854 describe manufacturing a reactive organopolysiloxane-polyoxyalkylene block copolymer having reactive functional groups by re-equilibrating, in the presence of an acid and a base, a polysiloxane having reactive functional groups with an organopolysiloxane-polyoxyalkylene block copolymer obtained via a hydrosilylation reaction of a polysiloxane having silicon-bonded hydrogen atoms on both molecular terminals and a polyoxyalkylene having silicon-bonded aliphatic unsaturated groups on both molecular terminals in the presence of a platinum catalyst.

PRIOR ART DOCUMENTS

Patent Documents

Patent Document 1: Japanese Unexamined Patent Application Publication No. H-04-211605
Patent Document 2: Japanese Unexamined Patent Application Publication No. H-04-234307
Patent Document 3: Japanese Unexamined Patent Application Publication No. H-09-268230
Patent Document 4: Japanese Unexamined Patent Application Publication No. H-05-310944
Patent Document 5: Japanese Unexamined Patent Application Publication No. H-09-151119
Patent Document 6: Japanese Unexamined Patent Application Publication No. H-09-183854

SUMMARY OF INVENTION

Technical Problem

With the conventional manufacturing methods described above, the degree of polymerization of the obtained organopolysiloxane-polyoxyalkylene block copolymer varies depending on the molar ratio of the silicon-bonded hydrogen atoms to the silicon-bonded aliphatic unsaturated groups. Moreover, in order to obtain a high molecular weight copolymer, it is necessary that the molar ratio be close to 1.0. However, in cases where a high molecular weight polysiloxane or polyoxyalkylene is used as a raw material, accurate quantitative determination of the molar amount of the silicon-bonded hydrogen atoms and the molar amount of the silicon-bonded aliphatic unsaturated groups is not easy due to the molecular weight distribution. Thus, precise control of the molar ratio of the silicon-bonded hydrogen atom to the aliphatic unsaturated groups is difficult and, in some cases, it is actually difficult to manufacture an organopolysiloxane-polyoxyalkylene block copolymer with a high degree of polymerization.

Additionally, in cases when the copolymer is manufactured by re-equilibrating a reactive organopolysiloxane-polyoxyalkylene block copolymer, the siloxane bonds are broken and reformed due to the effects of the acid or the base. As a result, it is even more difficult to increase the degree of polymerization of the organopolysiloxane-polyoxyalkylene block copolymer and, moreover, there is a problem in that low molecular weight cyclic polysiloxane is produced as a by-product. Low molecular weight cyclic polysiloxane is volatile and, therefore, vaporizes in the air and may contact the electronics or electric circuits of semiconductor devices or the like, thereby causing contact faults or, alternatively, vaporizes when applied to the skin and may cause a feeling of dryness or other unpleasant feeling.

An object of the present invention is to easily manufacture a high molecular weight organopolysiloxane-polyoxyalkylene block copolymer.

Additionally, another object of the present invention is to provide a manufacturing method for an organopolysiloxane-polyoxyalkylene block copolymer where an amount of volatile cyclic polysiloxane produced as a by-product is small.

Solution To Problem

The objects of the present invention are achieved by a manufacturing method for an organopolysiloxane-polyoxyalkylene block copolymer comprising a unit obtained by reacting: (A) a polyoxyalkylene compound represented by formula (1) below:

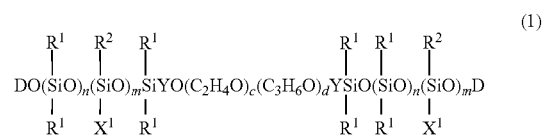

[wherein:
$R^1$ are each independently a substituted or unsubstituted, straight, branched, or cyclic monovalent hydrocarbon group having from 1 to 30 carbons and that is free of unsaturated aliphatic bonds, a hydroxyl group (limited to when D is a hydrogen atom), or an alkoxy group having from 1 to 30 carbons;

$R^2$ are each independently $R^1$ or $X^1$;

$X^1$ are each independently a reactive functional group represented by —$R^3$—$Z^1$ (where $R^3$ is directly bonded or is a substituted or unsubstituted, straight or branched divalent hydrocarbon group having from 1 to 20 carbons; and $Z^1$ is an amino group-containing group or an ammonium group-containing group);

D are each independently a hydrogen atom or a group selected from group represented by the formula below:

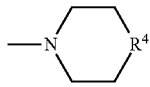

(wherein $R^4$ is an oxygen atom, a sulfur atom, or a divalent organic group) and —$N(R^5)_2$ (where $R^5$ are each independently a hydrogen atom or a substituted or unsubstituted straight, branched, or cyclic monovalent hydrocarbon group having from 1 to 30 carbons);

Y are each independently a substituted or unsubstituted, straight or branched divalent organic group having from 1 to 20 carbons;

c is a number not less than 2;

d is a number not less than 0; and m are each independently a number not less than 0, n are each independently a number not less than 1, and m+n is a number in a range from 1 to 10,000]; and (B) a polyorganosiloxane represented by the following formula (2):

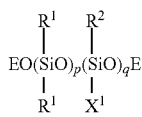

[wherein:

$R^1$, $X^1$, and $R^2$ are synonymous with those described above (however, only when E is a hydrogen atom, $R^1$ may be a hydroxyl group);

when the D moiety in formula (1) above is a hydrogen atom, E is represented by the following formula:

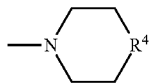

(wherein $R^4$ is synonymous with that described above) or —$N(R^5)_2$ (wherein $R^5$ is synonymous with that described above), and when the D moiety in formula (1) above is a group other than a hydrogen atom, E is a hydrogen atom; and p is a number not less than 1, q is a number not less than 0, and p+q is a number in a range from 1 to 10,000];

wherein the unit is represented by the following formula (3):

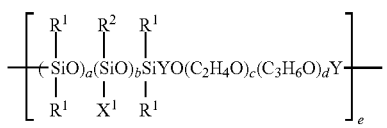

[wherein $R^1$, $R^2$, $X^1$, Y, c, and d are synonymous with those described above;

a is a number not less than 1, b is a number not less than 0, and a+b is a number in a range from 1 to 10,000; and e is a number not less than 1].

In the above formula, the divalent organic group moiety $R^4$ is preferably —$N(R^6)$— (wherein $R^6$ is a hydrogen atom or a substituted or unsubstituted, straight, branched, or cyclic monovalent hydrocarbon group having from 1 to 30 carbons); a substituted or unsubstituted, straight or branched divalent hydrocarbon group having from 1 to 20 carbons; or a substituted or unsubstituted, straight or branched divalent hydrocarbon group comprising at least one hetero-atom and having from 1 to 20 carbons.

In the above formula, the $R^5$ moiety is preferably an alkyl group having from 1 to 6 carbons.

In the above formula, c+d is preferably at least 4.

In the above formula, a weight average molecular weight of a polyoxyalkylene block represented by $(C_2H_4O)_c(C_3H_6O)_d$ is preferably from 200 to 15,000.

In the above formula, a and/or e is preferably a number not less than 2.

With the present invention, more preferably, (C) a polyorganosiloxane represented by the following formula (4) is reacted in addition to the polyoxyalkylene compound (A) and the polyorganosiloxane (B):

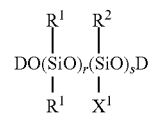

[wherein:

$R^1$, $X^1$, $R^2$, and D are synonymous with those described above (however, only when D is a hydrogen atom, $R^1$ may be a hydroxyl group); and r is a number not less than 1, s is a number not less than 0, and r+s is a number in a range from 1 to 10,000].

As necessary, water or an alcohol may be added during the reaction or after the reaction.

An acid is preferably added before the reaction, during the reaction, or after the reaction. Here, "adding the acid before the reaction" means adding the acid beforehand to the polyoxyalkylene compound (A) and/or the polyorganosiloxane (B), before reacting the polyoxyalkylene compound (A) and the polyorganosiloxane (B). Additionally, in cases where the polyorganosiloxane (C) is used, the acid may be added beforehand to the polyorganosiloxane (C). The acid may be an inorganic acid or an organic acid. A preferable example of an organic acid is carboxylic acid.

The present invention also relates to an organopolysiloxane-polyoxyalkylene block copolymer obtained via the manufacturing method described above.

A weight average molecular weight of the organopolysiloxane-polyoxyalkylene block copolymer is preferably not less than 50,000.

The present invention also relates to an emulsion and a cosmetic composition, particularly a hair cosmetic composition, comprising the organopolysiloxane-polyoxyalkylene block copolymer.

Advantageous Effects of Invention

With the manufacturing method for an organopolysiloxane-polyoxyalkylene block copolymer of the present invention, a high molecular weight organopolysiloxane-polyoxyalkylene block copolymer can be easily manufactured.

Additionally, with the manufacturing method for an organopolysiloxane-polyoxyalkylene block copolymer of the present invention, the amount of volatile cyclic polysiloxane produced as a by-product is small. Thus, the molecular weight of the organopolysiloxane-polyoxyalkylene block copolymer of the present invention is high and the content of volatile cyclic polysiloxane is low.

The organopolysiloxane-polyoxyalkylene block copolymer of the present invention and a composition comprising said copolymer can be used in various applications such as a mold release agent, a release agent for rubber product, a coating for release paper, a coating for fabric, an aqueous paint, a fiber treatment agents, and the like. Additionally, because the content of volatile cyclic polysiloxane is low and a high molecular weight organopolysiloxane is comprised, the organopolysiloxane-polyoxyalkylene block copolymer of the present invention and a composition comprising said copolymer can be preferably used in semiconductor devices and similar electric/electronic applications, and cosmetic composition applications.

The cosmetic composition of the present invention has a low content of volatile cyclic polysiloxane and, furthermore, comprises a high molecular weight organopolysiloxane. Therefore, superior cosmetic characteristics can be exhibited

DESCRIPTION OF EMBODIMENTS

The manufacturing method for an organopolysiloxane-polyoxyalkylene block copolymer of the present invention is characterized by reacting (A) a polyoxyalkylene compound having a particular chemical structure and (B) a polyorganosiloxane having a particular chemical structure. Next, description of the component (A) and the component (B) will be given.

Component (A)

A polyoxyalkylene compound (component (A)) represented by the following formula (1) is used as a raw material in the manufacturing method for an organopolysiloxane-polyoxyalkylene block copolymer of the present invention.

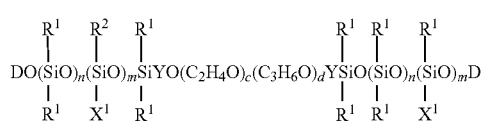

In this formula:
$R^1$ are each independently a substituted or unsubstituted, straight, branched, or cyclic monovalent hydrocarbon group having from 1 to 30 carbons and that is free of unsaturated aliphatic bonds, a hydroxyl group (limited to when D is a hydrogen atom), or an alkoxy group having from 1 to 30 carbons;
$R^2$ are each independently $R^1$ or $X^1$;
$X^1$ are each independently a reactive functional group represented by $-R^3-Z^1$ (where $R^3$ is directly bonded or is a substituted or unsubstituted, straight or branched divalent hydrocarbon group having from 1 to 20 carbons; and $Z^1$ is an amino group-containing group or an ammonium group-containing group);
D are each independently a hydrogen atom or a group selected from a group represented by the formula below:

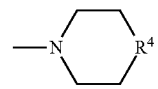

(wherein $R^4$ is an oxygen atom, a sulfur atom, or a divalent organic group) and $-N(R^5)_2$ (where $R^5$ are each independently a hydrogen atom or a substituted or unsubstituted straight, branched, or cyclic monovalent hydrocarbon group having from 1 to 30 carbons);
Y are each independently a substituted or unsubstituted, straight or branched divalent organic group having from 1 to 20 carbons;
c is a number not less than 2;
d is a number not less than 0; and
n are each independently a number not less than 1, m are each independently a number not less than 0 and n+m is a number in a range from 1 to 10,000.

The substituted or unsubstituted, straight, branched, or cyclic monovalent hydrocarbon group having from 1 to 30 carbons and that is free of unsaturated aliphatic bonds ($R^1$) is, for example, a monovalent saturated hydrocarbon group having preferably from 1 to 20 carbons, more preferably from 1 to 10 carbons, and even more preferably from 1 to 4 carbons; or a monovalent aromatic hydrocarbon group having preferably from 6 to 20 carbons, more preferably from 6 to 12 carbons, and even more preferably from 6 to 8 carbons.

Examples of the monovalent saturated hydrocarbon group include straight or branched alkyl groups such as methyl groups, ethyl groups, n-propyl groups, isopropyl groups, n-butyl groups, isobutyl groups, sec-butyl groups, tert-butyl groups, pentyl groups, hexyl groups, heptyl groups, octyl groups, nonyl groups, decyl groups, and the like; and cycloalkyl groups such as cyclopentyl groups, cyclohexyl groups, cycloheptyl groups, cyclooctyl groups, and the like. Of these, a straight or branched alkyl group having from 1 to 4 carbons is preferable and a methyl group is particularly preferable.

Examples of the monovalent aromatic hydrocarbon group include aryl groups such as phenyl groups, tolyl groups, xylyl groups, mesityl groups, and the like. Of these, a phenyl group is preferable. Note that in the present specification, "aromatic hydrocarbon group" includes groups in which an aromatic hydrocarbon and a saturated hydrocarbon are conjugated in addition to groups formed only from an aromatic hydrocarbon. Examples of groups in which an aromatic hydrocarbon and a saturated hydrocarbon are conjugated include aralkyl groups such as benzyl groups, phenethyl groups, and the like.

The hydrogen atom on the monovalent hydrocarbon group described above may be substituted by one or more substituents, and said substituent may, for example, be a halogen atom (i.e. a fluorine atom, a chlorine atom, a bromine atom, and an iodine atom); a reactive functional group selected from the group consisting of mercapto groups, epoxy groups, amide groups, ester groups, (meth)acryloxy groups, and isocyanate groups; or a monovalent hydrocarbon group having said reactive functional group. Examples of the substituted monovalent hydrocarbon group include 3,3,3-trifluoropropyl groups, 3-chloropropyl groups, 3-mercaptopropyl groups, 2,3-epoxypropyl groups, 3,4-epoxybutyl groups, 4,5-epoxypentyl groups, 2-glycidoxyethyl groups, 3-glycidoxypropyl groups, 4-glycidoxybutyl groups, 2-(3,4-epoxycyclohexyl) ethyl groups, 3-(3,4-epoxycyclohexyl)propyl groups, 3-isocyanate propyl groups, and the like. Note that a reactive functional group having an acidic group such as a carboxyl group, a carbinol group, or the like, or an alcoholic hydroxy group is not preferable as the substituent because such a reactive functional group is reactive with respect to aminoxy groups.

Examples of the alkoxy group having from 1 to 30 carbons include methoxy groups, ethoxy groups, propoxy groups, butoxy groups, isopropenyloxy groups, methoxy ethoxy groups, phenyloxy groups, acetoxy groups, cyclohexyloxy groups, dodecanyloxy groups, and the like. Alkoxy groups having from 1 to 12 carbons are preferable, alkoxy groups having from 1 to 8 carbons are more preferable, and alkoxy groups having from 1 to 6 carbons are even more preferable. Methoxy groups and ethoxy groups are particularly preferable.

Examples of the substituted or unsubstituted, straight or branched divalent hydrocarbon group having from 1 to 20 carbons ($R^3$) include methylene groups, dimethylene groups, trimethylene groups, tetramethylene groups, pentamethylene groups, hexamethylene groups, heptamethylene groups, octamethylene groups, and similar straight or branched alkylene groups having from 1 to 20 carbons; vinylene groups, allylene groups, butenylene groups, hexenylene groups, octenylene groups, and similar alkenylene groups having from 2 to 20 carbons; phenylene groups, diphenylene groups, and similar arylene groups having from 6 to 20 carbons; dimethylenephenylene groups and similar alkylene-arylene groups having from 7 to 20 carbons; and groups wherein the hydrogen atoms bonded to the carbon atoms of these groups are substituted at least partially by fluorine or a similar halogen atom. The divalent hydrocarbon group is preferably a straight or branched alkylene group having from 1 to 20 carbons, and is particularly preferably an ethylene (dimethylene) group or a propylene (trimethylene) group.

The amino group-containing group is not particularly limited provided that it has at least one amino group, and is preferably a group represented by the following formula.

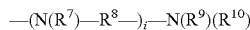
—$(N(R^7)$—$R^8$—$)_i$—$N(R^9)(R^{10})$

In this formula, $R^7$, $R^9$, and $R^{10}$ are each independently a hydrogen atom; a substituted or unsubstituted straight, branched, or cyclic monovalent hydrocarbon group having from 1 to 30 carbons; or —$COR^{11}$ (where $R^{11}$ is a hydrogen atom or a substituted or unsubstituted straight, branched, or cyclic monovalent hydrocarbon group having from 1 to 30 carbons.

$R^8$ is a substituted or unsubstituted straight or branched divalent hydrocarbon group having from 1 to 20 carbons. i is an integer from 0 to 5, and preferably an integer from 0 to 3.

The substituted or unsubstituted, straight, branched, or cyclic monovalent hydrocarbon groups having from 1 to 30 carbons ($R^7$, $R^9$, $R^{10}$, and $R^{11}$ moieties), for example, are monovalent saturated hydrocarbon groups having preferably from 1 to 20 carbons, more preferably from 1 to 10 carbons, and even more preferably from 1 to 4 carbons; monovalent unsaturated aliphatic hydrocarbon groups having preferably from 2 to 20 carbons, more preferably from 2 to 10 carbons, and even more preferably from 2 to 4 carbons; or monovalent aromatic hydrocarbon groups having preferably from 6 to 20 carbons, more preferably from 6 to 12 carbons, and even more preferably from 6 to 8 carbons.

The definitions and specific examples of the monovalent saturated hydrocarbon group and the monovalent aromatic hydrocarbon group are as recited above. Examples of the monovalent unsaturated aliphatic hydrocarbon group include straight or branched alkenyl groups such as vinyl groups, 1-propenyl groups, allyl groups, isopropenyl groups, 1-butenyl groups, 2-butenyl groups, pentenyl groups, hexenyl groups, and the like; cycloalkenyl groups such as cyclopentenyl groups, cyclohexenyl groups, and the like; and, furthermore, cycloalkenylalkyl groups such as cyclopentenylethyl groups, cyclohexenylethyl groups, cyclohexenylpropyl groups, and the like. Of these, a straight or branched alkenyl group is preferable and a vinyl group is particularly preferable.

The definition and specific examples of the substituted or unsubstituted straight or branched divalent hydrocarbon group having from 1 to 20 carbons ($R^8$) is as recited above.

The ammonium group-containing group is not particularly limited provided that it has at least one ammonium group, and is preferably a group represented by the following formula.

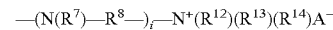
—$(N(R^7)$—$R^8$—$)_i$—$N^+(R^{12})(R^{13})(R^{14})A^-$

In this formula, $R^7$, $R^8$ and i are synonymous with those described above.

$R^{12}$, $R^{13}$, and $R^{14}$ are each independently a substituted or unsubstituted straight, branched, or cyclic monovalent hydrocarbon group having from 1 to 30 carbons.

$A^-$ is an anion.

The definition and specific examples of the substituted or unsubstituted, straight, branched, or cyclic monovalent hydrocarbon groups ($R^{12}$, $R^{13}$, and $R^{14}$) having from 1 to 30 carbons are as recited above.

The anion is not particularly limited provided that it is at least a monovalent anion, and preferable examples thereof include halide anions ($F^-$, $Cl^-$, $Br^-$, and $I^-$). Of these, a chloride anion ($Cl^-$) is particularly preferable.

Specific examples of $Z^1$ include —$NH_2$, —$NH(CH_2)_2NH_2$, —$N(CH_3)_2$, —$N(CH_3)(CH_2)_2N(CH_3)_2$, —$N^+(CH_3)_3Cl^-$, —$N(CH_3)(CH_2)_2N(CH_3)C$=$O(CH_3)$, and the like.

Preferable examples of $X^1$ include —$(CH_2)_3NH_2$, —$(CH_2)_3N(CH_3)_2$, —$(CH_2)_3N^+(CH_3)_3Cl^-$, —$(CH_2)_2NH$ $(CH_2)_2NH_2$, —$(CH_2)_3NH(CH_2)_2NH_2$, —$(CH_2)_3NH$ $(CH_2)_2N(CH_3)_2$, —$(CH_2)_3N(CH_3)(CH_2)_2N(CH_3)_2$, —$(CH_2)_3N(CH_3)(CH_2)_2N(CH_3)C$=$O(CH_3)$, —$(CH_2)_6NH$ $(CH_2)_2NH_2$, —$(CH_2)_3(NH(CH_2)_2)_2NH_2$, —$(CH_2)_3(NH$ $(CH_2)_2)_3NH_2$, —$(CH_2)_3NH(CH_2)_2N(C_4H_9)_2$, —$(CH_2)_3NH$ $(CH_2)_2NH(CH_2$—$C_6H_5)$, and the like.

When the D moiety in formula (1) above is a hydrogen atom, the polyoxyalkylene compound represented by formula (1) will have a hydroxyl group having silicon atoms at the molecular terminals.

On the other hand, when the D moiety in formula (1) above is a group represented by the formula (a):

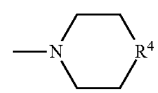

(a)

(wherein $R^4$ is an oxygen atom, a sulfur atom, or a divalent organic group); or a group represented by the formula (b): —$N(R^5)_2$ (b) (wherein $R^5$ are each independently a hydrogen atom or a substituted or unsubstituted straight, branched, or cyclic monovalent hydrocarbon group having from 1 to 30 carbons), the polyoxyalkylene compound represented by formula (1) will have an aminoxy group having silicon atoms at the molecular terminals.

The divalent organic group ($R^4$) is not particularly limited, but is preferably —$N(R^6)$— (wherein $R^6$ is a hydrogen atom or a substituted or unsubstituted, straight, branched, or cyclic monovalent hydrocarbon group having from 1 to 30 carbons); a substituted or unsubstituted, straight or branched divalent hydrocarbon group having from 1 to 20 carbons; or a substituted or unsubstituted, straight or branched divalent hydrocarbon group comprising at least one hetero-atom and having from 1 to 20 carbons.

The definition and specific examples of the substituted or unsubstituted, straight, branched, or cyclic monovalent hydrocarbon groups ($R^5$ and $R^6$) having from 1 to 30 carbons are as recited above. In the above formula, the $R^5$ and $R^6$ moieties are preferably alkyl groups having from 1 to 6 carbons.

The definition and specific examples of the substituted or unsubstituted straight or branched divalent hydrocarbon group having from 1 to 20 carbons is as recited above. The substituted or unsubstituted, straight or branched divalent hydrocarbon group comprising at least one hetero-atom and having from 1 to 20 carbons is not particularly limited provided that it comprises at least one hetero-atom such as an oxygen atom, a sulfur atom, a nitrogen atom, or the like, but preferably has a molecular skeleton formed from 3 to 17 carbon atoms, and 1 to 3 nitrogen atoms or 1 to 2 oxygen atoms. Examples thereof include —R—O—, —R—O—R'—, —R—CO—, —R—COO—, —R—COO—R'—, —R—CONH—, and —CH=N—R— (wherein R and R' are each independently a substituted or unsubstituted, straight or branched divalent hydrocarbon group having from 1 to 20 carbons). —CH=N—CH=CH— or —(CH$_2$)$_2$—O—(CH$_2$)$_2$— is particularly preferable.

The divalent organic group (Y) is a substituted or unsubstituted straight, branched, or cyclic divalent organic group having from 1 to 20 carbons, and is preferably a divalent hydrocarbon group or a divalent hydrocarbon group having at least one hetero-atom. Note that specific examples of the divalent hydrocarbon group or the divalent hydrocarbon group having at least one hetero-atom are as recited above. Y is preferably bonded to an adjacent silicon atom via a carbon-silicon bond, and is preferably bonded to the polyoxyalkylene block (—(C$_2$H$_4$O)$_c$—(C$_3$H$_6$O)$_d$—) via an adjacent oxygen atom.

c in formula (1) is preferably a number in a range from 2 to 1,000 and is more preferably a number in a range from 10 to 300. d in formula (1) is preferably a number in a range from 0 to 100 and is more preferably a number in a range from 0 to 10. Moreover, c+d is preferably at least 4, is more preferably not less than 6, is even more preferably in a range from 10 to 500, and is yet even more preferably in a range from 10 to 300.

m in formula (1) is preferably a number in a range from 0 to 100 and more preferably a number in a range from 1 to 10; and n is preferably a number in a range from 1 to 10,000 and more preferably a number in a range from 100 to 3,000.

The component (A) can be manufactured according to a conventionally known method. For example, when the D moiety in formula (1) is the group represented by formula (a) or formula (b) and the component (A) has a silicon-bonded aminoxy group, the component (A) can be synthesized by reacting a polyoxyalkylene having unsaturated groups at both molecular terminals and a polysiloxane having silicon-bonded hydrogen atoms at both molecular terminals in the presence of a platinum catalyst or the similar hydrosilylation reaction catalyst in order to synthesize a polyoxyalkylene having hydropolysiloxy groups at both molecular terminals; and reacting the resulting polyoxyalkylene with dialkylhydroxyamine in order to introduce an aminoxy group to the molecular terminal. On the other hand, when the D moiety in formula (1) is a hydrogen atom and the component (A) has a silicon-bonded hydroxyl group, the component (A) can be synthesized by hydrolyzing the polyoxyalkylene having hydropolysiloxy groups at both molecular terminals obtained according to the method described above in the presence of an acidic catalyst in order to replace the silicon-bonded hydrogen atoms at the molecular terminals with hydroxyl groups.

Component (B)

A polyorganosiloxane (component (B)) represented by the following formula (2) is used as a raw material in the manufacturing method for an organopolysiloxane-polyoxyalkylene block copolymer of the present invention.

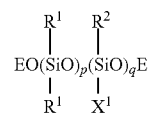

(2)

In this formula:

$R^1$, $X^1$, and $R^2$ are synonymous with those described above (however, only when E is a hydrogen atom, $R^1$ may be a hydroxyl group);

when the D moiety in formula (1) above is a hydrogen atom, E is represented by the following formula:

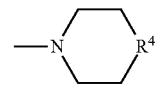

(wherein $R^4$ is synonymous with that described above) or —N($R^5$)$_2$ (wherein $R^5$ is synonymous with that described above), and when the D moiety in formula (1) above is a group other than a hydrogen atom, E is a hydrogen atom; and p is a number not less than 1, q is a number not less than 0, and p+q is a number in a range from 1 to 10,000.

In formula (2), p is preferably a number in a range from 1 to 10,000 and preferably a number in a range from 100 to 3,000; and q is preferably a number in a range from 0 to 100 and more preferably a number in a range from 1 to 10.

As is clear from the definitions given above, when the component (A) has silicon-bonded hydroxyl groups at the molecular terminals, the component (B) has silicon-bonded aminoxy groups at the molecular terminals. Additionally, when the component (A) has silicon-bonded aminoxy groups at the molecular terminals, the component (B) has silicon-bonded hydroxyl groups at the molecular terminals.

Component (C)

In the present invention, in addition to the component (A) and the component (B), a polyorganosiloxane (C) represented by the following formula (4) may be further reacted.

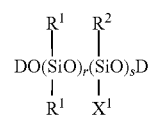

(4)

In this formula:

$R^1$, $X^1$, $R^2$, and D are synonymous with those described above (however, only when D is a hydrogen atom, $R^1$ may be a hydroxyl group); and r is a number not less than 1, s is a number not less than 0, and r+s is a number in a range from 1 to 10,000.

In formula (4), r is preferably a number in a range from 1 to 10,000, and more preferably a number in a range from 100 to 3,000; and s is preferably a number in a range from 0 to 100, and more preferably a number in a range from 1 to 10.

In the present invention, the organopolysiloxane-polyoxyalkylene block copolymer is manufactured via a condensation reaction of the component (A), the component (B), and optionally, the component (C). Silicon-bonded hydroxyl groups and silicon-bonded aminoxy groups absolutely exist in either of these components and, therefore, the component (A), the component (B), and optionally, the component (C) are connected and the polymer chain is elongated as a result of the condensation reaction.

The organopolysiloxane-polyoxyalkylene block copolymer obtained by reacting the component (A), the component (B), and optionally, the component (C) is represented by the following formula (3).

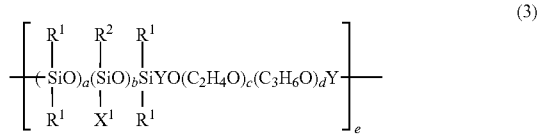

(3)

In this formula, $R^1$, $R^2$, $X^1$, Y, c, and d are synonymous with those described above;
a is a number not less than 1, b is a number not less than 0, and a+b is a number in a range from 1 to 10,000; and
e is a number not less than 1.

In formula (3), a is preferably a number not less than 2, is more preferably a number in a range from 2 to 10,000, and is even more preferably a number in a range from 100 to 3,000. Additionally, b is preferably a number in a range from 0 to 100, and is more preferably a number in a range from 1 to 10.

In formula (3), e is preferably a number not less than 2, is more preferably a number not less than 5, is even more preferably a number not less than 10, is yet even more preferably in a range from 10 to 100,000, and is particularly preferably in a range from 100 to 10,000.

A content of the polyoxyalkylene block (—$(C_2H_4O)_a$—$(C_3H_6O)_b$—) in the block copolymer is preferably from 30 to 95 wt %, and more preferably from 40 to 85 wt %. Additionally, preferably not less than 60 wt % and more preferably not less than 70 wt % of the polyoxyalkylene block is constituted by polyoxyethylene groups. A weight average molecular weight of the polyoxyalkylene block is preferably from 200 to 15,000.

The manufacturing method for an organopolysiloxane-polyoxyalkylene block copolymer of the present invention can be performed under any conditions because the condensation reaction of the component (A) with the component (B) is carried out easily. For example, the organopolysiloxane-polyoxyalkylene block copolymer can be produced via a condensation reaction of the component (A) and the component (B) by simply adding and mixing the component (B) in a reaction system including the component (A). Alternately, the component (A) may be added and mixed with a reaction system including the component (B). The condensation reaction of the component (A) and the component (B) begins after both components are added and mixed, but the reaction system is preferably agitated so that the reaction is carried out uniformly. Additionally, a reaction temperature and reaction time of the condensation reaction are not particularly limited and, for example, the reaction can be sufficiently carried out by agitating or allowing the reaction system to sit at rest at room temperature for a number of days. Moreover, the component (C) can be optionally added to the reaction system.

Usage amounts of the component (A) and the component (B) can be selected as desired and, for example, from 1 to 10,000 parts by weight, preferably from 10 to 1,000 parts by weight, and more preferably from 50 to 500 parts by weight of the component (B) can be used per 100 parts by weight of the component (A). However, in order to reduce the amount of unreacted reactant, a relative amount of the silicon-bonded aminoxy group, preferably in a range from 0.8 to 1.2 mol and more preferably in a range from 0.9 to 1.1 mol per 1 mol of the silicon-bonded hydroxyl group is used.

A usage amount of the component (C) can be selected as desired and, for example, from 1 to 10,000 parts by weight, preferably from 10 to 1,000 parts by weight, and more preferably from 10 to 100 parts by weight of the component (C) can be used per 100 parts by weight of the component (A). Additionally, from 1 to 100 parts by weight, preferably from 10 to 100 parts by weight, and more preferably from 50 to 100 parts by weight of the component (C) may be used per 100 parts by weight of the component (B).

The molecular weight of the organopolysiloxane-polyoxyalkylene block copolymer of the present invention that is obtained via the condensation reaction of the component (A), the component (B), and optionally, the component (C) is high, having a weight average molecular weight of not less than, for example, 50,000. The weight average molecular weight of the organopolysiloxane-polyoxyalkylene block copolymer of the present invention preferably is from 50,000 to 1,000,000, more preferably from 50,000 to 800,000, even more preferably from 90,000 to 700,000, and yet even more preferably from 100,000 to 600,000. Additionally, a viscosity of the organopolysiloxane-polyoxyalkylene block copolymer is in a range from 100,000 to 5,000,000 and preferably from 200,000 to 3,000,000 mm$^2$/s.

Thus, the organopolysiloxane-polyoxyalkylene block copolymer obtained via the present invention has a high molecular weight and, therefore, can, for example, exhibit superior properties as a raw material for use in cosmetic compositions.

Additionally, with the present invention, an amount of low molecular weight cyclic siloxanes such as octamethylcyclotetrasiloxane, decamethylcyclopentasiloxane, dodecamethylcyclohexasiloxane, and the like, which is a by-product of the condensation reaction, is small. These low molecular weight cyclic siloxanes are volatile and, particularly when applied to the skin and vaporize, may cause discomfort such as a feeling of dryness. However, the content of such volatile cyclic polysiloxanes is low in the organopolysiloxane obtained according to the present invention and, therefore, from the perspective of feeling during use, is suitable as a raw material for use in cosmetic compositions.

When reacting the component (A), the component (B), and optionally, the component (C), the use of a reaction medium such as a solvent or dispersing medium is not necessary but, for example, in cases where the viscosity of the obtained copolymer is excessively high or, alternately, in cases where it is necessary to increase the dispersibility of the components, a reaction medium such as an inert solvent, a dispersing medium, or the like may be used in the reaction. The inert reaction medium preferably does not have a hydroxyl group, and examples of such reaction media include low viscosity polysiloxanes, aliphatic hydrocarbons, aromatic hydrocarbons, ester oils, and the like that do not have a hydroxyl group.

The reaction of the component (A), the component (B), and optionally, the component (C) can be stopped by adding water, an alcohol, or a mixture thereof, or a similar compound that can hydrolyze the aminoxy groups to the reaction system. Thus, with the present invention by adding, for example, water or an alcohol to the reaction system during the reaction of the component (A), the component (B), and optionally, the component (C), an organopolysiloxane-polyoxyalkylene block copolymer having a desired viscosity (degree of polymerization) can be obtained. The alcohol preferably has from 1 to 5 carbons and more preferably has from 1 to 3 carbons. Additionally, as a result, the aminoxy groups remaining in the organopolysiloxane-polyoxyalkylene block copolymer will be hydrolyzed and, therefore, stability of the viscosity of the copolymer can be improved.

After completion of the reaction, preferably the hydroxy amine by-product (diethylhydroxyamine and the like) is removed by heating under reduced pressure and/or neutralized using an acid. As a result, the odor particular to hydroxyamines can be reduced. Thus, with the present invention, the acid is preferably added to the raw material or to the reaction system before, during and after the reaction of the component (A), the component (B), and optionally, the component (C). Either water dispersible or water soluble acid can be used as the acid, but a water soluble acid is preferable.

The acid is preferably a water soluble acid. The water soluble acid is not particularly limited provided that it can be dissolved in water, and is preferably an Arrhenius acid, which emits protons into an aqueous solution.

The acid may be an inorganic acid, an organic acid, or a mixture of an inorganic acid and an organic acid. Additionally, more than one of each of an inorganic acid and an organic acid can be used.

The inorganic acid is not particularly limited, and examples thereof include hydrochloric acid, sulfuric acid, nitric acid, phosphoric acid, carbonic acid, boric acid, and the like. Note that in the present specification, "phosphoric acid" includes alkyl phosphoric acid, and "sulfuric acid" includes alkyl sulfuric acid.

The organic acid is not particularly limited, and can be a monocarboxylic acid (including monohydroxy monocarboxylic acid and dihydroxy monocarboxylic acid), a dicarboxylic acid (including monohydroxy dicarboxylic acid and dihydroxy dicarboxylic acid), a polycarboxylic acid, or a similar carboxylic acid. Examples thereof include:

Straight saturated aliphatic monocarboxylic acids (alkanoic acids) such as formic acid, acetic acid, propionic acid, butyric acid, valeric acid, caproic acid, enanthic acid, caprylic acid, pelargonic acid, capric acid, undecanoic acid, and the like;

Branched saturated aliphatic monocarboxylic acids (alkanoic acids) such as 2-methylpropanoic acid, 2-methylbutanoic acid, trimethylpropanoic acid, 2-methylpentanoic acid, trimethyl acetic acid, and the like;

Unsaturated aliphatic monocarboxylic acids (alkenoic acids) such as acrylic acid, methacrylic acid, crotonic acid, isocrotonic acid, vinyl acetic acid, allyl acetic acid, hexenoic acid, heptenoic acid, octenoic acid, and the like;

Unsaturated aliphatic monocarboxylic acids (alkynoic acids) such as propiolic acid, tetrolic acid, allyl acetic acid, hexynoic acid, octynoic acid, and the like;

Polyunsaturated aliphatic monocarboxylic acids such as pentadienoic acid, sorbic acid, and the like;

α-hydroxymonocarboxylic acids such as citric acid, lactic acid, glycolic acid, α-oxybutyric acid, and the like;

β-hydroxymonocarboxylic acids such as 2-hydroxyvaleric acid, 2-hydroxycaproic acid, β-oxybutyric acid, and the like;

γ-hydroxymonocarboxylic acids such as γ-oxybutyric acid and the like;

Dihydroxymonocarboxylic acids such as glyceric acid and the like;

Other hydroxymonocarboxylic acids such as hydroxy(meth)acrylic acid and the like;

Saturated aliphatic dicarboxylic acids such as oxalic acid, malonic acid, succinic acid, glutaric acid, adipic acid, and the like;

Monohydroxy saturated aliphatic dicarboxylic acids such as tartronic acid, malic acid, and the like;

Dihydroxy saturated aliphatic dicarboxylic acids such as tartaric acid and the like;

Unsaturated aliphatic dicarboxylic acids such as maleic acid, fumaric acid, and the like;

Aromatic monocarboxylic acid such as benzoic acid and the like;

Aromatic dicarboxylic acids such as phthalic acid and the like;

Amino acids such as glycine, alanine, valine, leucine, glutamic acid, aspartic acid, PL-pyrrolidone carboxylic acid, and the like; and Polycarboxylic acids such as gallic acid and the like.

A usage amount of the acid can be selected as desired and, for example, from 0.001 to 10 parts by weight, preferably from 0.01 to 5 parts by weight, and more preferably from 0.1 to 1 parts by weight of the acid can be used per 100 parts by weight of the component (A) or the component (B).

With the present invention, the component (A), the component (B), and optionally, the component (C) may be emulsified in water using a surfactant and, thereafter the condensation reaction may be carried out. As a result, an emulsion of the organopolysiloxane-polyoxyalkylene block copolymer can be obtained. In this case, preferably the component (A), the component (B), and optionally, the component (C) are emulsified using a surfactant and, thereafter, the condensation reaction is carried out for a predetermined time.

The surfactant is not particularly limited, and at least one type can be selected from the group consisting of anionic surfactants, cationic surfactants, nonionic surfactants, amphoteric surfactants, and semipolar surfactants.

Examples of the anionic surfactants include saturated or unsaturated fatty acid salts (e.g. sodium laurate, sodium stearate, sodium oleate, sodium linolenate, and the like); alkylsulfuric acid salts; alkylbenzene sulfonic acids (e.g. hexylbenzenesulfonic acid, octylbenzenesulfonic acid, dodecylbenzenesulfonic acid, and the like) and salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl- or alkenylsulfuric acid salts; alkylamide sulfuric acid salts; alkyl- or alkenyl phosphoric acid salts; alkylamide phosphoric acid salts; alkyloylalkyl taurine salts; N-acylamino acid salts; sulfosuccinic acid salts; alkyl ether carboxylic acid salts; amide ether carboxylic acid salts; α-sulfofatty acid ester salts; alanine derivatives; glycine derivatives; and arginine derivatives. Examples of salts include alkali metal salts such as sodium salts and the like, alkaline earth metal salts such as magnesium salts and the like, alkanolamine salts such as triethanolamine salts and the like, and ammonium salts.

Examples of cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium (2 EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, diethylaminoethylamide stearate, dimethylaminopropylamide stearate, behenic acid amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

Examples of nonionic surfactants include polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethylenegly col, polyoxyalkylene-modified silicones, polyglyceryl-modified silicones, glyceryl-modified silicones, sugar-modified silicones, fluorine-based surfactants, polyoxyethylene/polyoxypropylene block polymers, and alkyl polyoxyethylene/polyoxypropylene block polymer ethers. Additionally, as necessary, polyoxyalkylene-modified silicones, polyglyceryl-modified silicones, and glyceryl-modified silicones in which an alkyl branch, a straight chain silicone branch, a siloxane dendrimer branch, or the like is provided with the hydrophilic group can be suitably used.

Examples of amphoteric surfactants include imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specifically, imidazoline-type amphoteric surfactants such as 2-undecyl-N,N,N-(hydroxyethylcarboxymethyl)-2-imidazoline sodium, 2-cocoyl-2-imidazolinium hydroxide-1-carboxyethyloxy disodium salt, and the like; alkylbetaine-type amphoteric surfactants such as lauryl dimethylaminoacetic betaine, myristyl betaine, and the like; amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric acid amidopropyl dimethylamino acetic acid betaine, myristic acid amidopropyl dimethylamino acetic acid betaine, palmitic acid amidopropyl dimethylamino acetic acid betaine, stearic acid amidopropyl dimethylamino acetic acid betaine, oleic acid amidopropyl dimethylamino acetic acid betaine, and the like; alkylsulfobetaine-type amphoteric surfactants such as coconut oil fatty acid dimethyl sulfopropyl betaine and the like; alkyl hydroxy sulfobetaine-type amphoteric surfactants such as lauryl dimethylaminohydroxy sulfobetaine and the like; phosphobetaine-type amphoteric surfactants such as laurylhydroxy phosphobetaine and the like; and amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine, and the like.

Examples of semipolar surfactants include alkylamine oxide-type surfactants, alkylamine oxides, alkylamide amine oxides, alkylhydroxyamine oxides, and the like. Alkyldimethylamine oxides having from 10 to 18 carbons, alkoxyethyl dihydroxyethylamine oxides having from 8 to 18 carbons, and the like are preferably used. Specific examples thereof include dodecyldimethylamine oxide, dimethyloctylamine oxide, diethyldecylamine oxide, bis-(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide. A content of the surfactant is not particularly limited and, for example, can be in a range from 0.1 to 50 wt % (mass %) and preferably a range from 1 to 20 wt % (mass %) of the composition comprising all of the components.

The composition can also comprise water. A content of the water is not particularly limited and, for example, can be in a range from 10 to 90 wt % (mass %) of the composition.

The composition preferably comprises the acid described above. A concentration of the acid is not particularly limited and, for example, preferably is in a range from 0.001 to 10 wt %, more preferably is in a range from 0.01 to 5 wt %, and even more preferably is in a range from 0.1 to 1 wt % of the entire composition. In cases where the acid is compounded, the pH of the composition is preferably not more than 8, more preferably not more than 7.5, and even more preferably not more than 7.

The emulsifying of the component (A), the component (B), and optionally, the component (C) and the condensation reaction thereafter can be performed using conventionally known methods. For example, the emulsifying and condensation reaction can be performed by uniformly mixing the component (A), the component (B), optionally the component (C), the surfactant, and optionally, a small amount of the water; thereafter stirring and emulsifying the mixture using an emulsifier such as a colloid mill, a line mill, a homomixer, or the like; and then adding water and uniformly stirring/dispersing the emulsion therein. As necessary, the emulsion may be further stabilized by stirring/emulsifying using an emulsifier such as a homogenizer or the like. It is not necessary to heat the reaction system because the condensation reaction of the component (A), the component (B), and optionally, the component (C) proceeds at room temperature. However, if necessary, the reaction system may be heated to a temperature of, for example, 50 to 70° C. As a result, the reaction can be completed in 30 minutes to 12 hours.

With the emulsion obtained as described above, a high molecular weight organopolysiloxane-polyoxyalkylene block copolymer is typically dispersed in an aqueous phase. The amount of volatile cyclic polysiloxane in the copolymer is small and, in cases where the acid is used, unpleasant odor is reduced. Therefore, the emulsion can be used as-is as a raw material for a cosmetic composition.

A concentration of the organopolysiloxane-polyoxyalkylene block copolymer in the emulsion of the present invention is not particularly limited, but is preferably in a range from 5 to 60 wt % and more preferably in a range from 10 to 50 wt % of the entire emulsion.

The emulsion of the present invention comprises the high molecular weight organopolysiloxane-polyoxyalkylene block copolymer having the chain elongated due to the condensation reaction of the component (A), the component (B), and optionally, the component (C) and, the content of volatile cyclic polysiloxanes is low. Therefore, can be preferably used in cosmetic composition applications. Furthermore, in cases where the acid is used, the unpleasant odor originating from the hydroxyamine that is produced as a by-product is reduced and, therefore, the emulsion is more preferable as a raw material for a cosmetic composition.

The organopolysiloxane-polyoxyalkylene block copolymer of the present invention or an emulsion or similar composition comprising the same can be compounded in a cosmetic composition. A compounded amount thereof is not particularly limited and, for example, can be in a range from 1 to 99 wt %, 10 to 90 wt %, or 20 to 80 wt % of the cosmetic composition.

The cosmetic composition of the present invention can comprise other optional components. Examples of the optional components include oil agents, surfactants, water-soluble polymers, alcohols, thickening agents/gelling agents, powders, solid silicone resins or crosslinking organopolysiloxanes, acryl silicone dendrimer copolymers, ultraviolet light blocking components, oxidation hair colorants, direct dyes, moisturizing agents, preservatives, antimicrobial agents, perfumes, salts, oxidizing agents or antioxidants, chelating agents, refreshing agents, anti-inflammatory agents, and bioactive components (e.g. skin-lightening agents, cell activating agents, skin trouble improvers, circulation promoters, skin astringents, antiseborrheic agents, vitamins, amino acids, nucleic acids, hormones, and the like).

The type of cosmetic composition is not particularly limited, and specific examples of products include skin cosmetic composition products such as skin cleansing products, skin care cosmetic composition products, makeup cosmetic composition products, anti-perspirants, UV screening products, and the like; hair cosmetic composition products such as hair cleansing products, hair dressing products, hair coloring products, hair growth products, hair treatment products, and the like; and bath use products. Particularly, the cosmetic composition of the present invention comprises an organopolysiloxane having a high molecular weight and, therefore, is suitable as a hair cosmetic composition.

Specific examples of hair cosmetic compositions include shampoos, rinse-in shampoos, and similar hair cleansing agents; hair oils, hair waxes, hair use curl holding agents, setting agents, hair creams, hairsprays, hair liquids, and similar hair dressing products; hair coloring substances, temporary dyes, permanent dyes, and similar hair coloring products; hair tonics, hair treatment essences, hair packs, and similar hair growth products; hair rinses, hair conditioners, and similar hair treatment products.

The form of the cosmetic composition of the present invention is not particularly limited, and the cosmetic composition may be used in a W/O emulsion, O/W emulsion, liquid, solid, paste-like, gel-like, mousse-like, mist-like, granule, or similar form. Of these, the O/W emulsion form is preferable.

On the other hand, a film that is releasable, peelable, water repellent, stain repellent, and weather resistant can be formed by applying the organopolysiloxane-polyoxyalkylene block copolymer of the present invention or an emulsion or similar composition comprising said copolymer to an arbitrary substrate via a method such as spraying, rolling, brushing, immersing, or the like and, thereafter, allowing the substrate to sit at rest or heat drying the substrate. Therefore, the organopolysiloxane-polyoxyalkylene block copolymer of the present invention or the composition comprising said copolymer can also be used as a mold release agent, a release agent for rubber product, a coating agent for release paper, a fabric coating agent, an aqueous paint, a fiber treatment agent, or the like.

In this case, the composition can, as necessary, comprise an organic carboxylate of a metal such as iron, lead, antimony, cadmium, titanium, calcium, bismuth, zirconium, and the like; an organic amine compound such as triethanolamine, triethylenediamine, dimethylphenylamine, and the like; a preservative; a colorant; a resin processing agent such as glyoxal resin, melanin resin, urea resin, polyester resin, acrylic resin, and the like; a rubber latex such as a styrene-butadiene latex, a natural rubber, or the like; an emulsion of a fluororesin; an emulsion of an organohydrogenpolysiloxane; an emulsion of an organoalkoxysilane; and the like.

INDUSTRIAL APPLICABILITY

With the manufacturing method for an organopolysiloxane-polyoxyalkylene block copolymer of the present invention, an organopolysiloxane having low content of volatile cyclic polysiloxane and having a high molecular weight can be easily manufactured. Thus, the copolymer obtained according to the present invention and the emulsion comprising said copolymer can be used in various conventional applications such as a mold release agent, a release agent for rubber product, a coating for release paper, a fabric coating, an aqueous paint, a fiber treatment agents, and the like and, furthermore can be used in applications that have been impossible to-date due to the effects of the volatile cyclic polysiloxane. For example, the copolymer obtained according to the present invention and the emulsion comprising said copolymer can be used in electric/electronic applications and the like, and also as a raw material of a cosmetic composition or the like for use on the human body.

Additionally, the low content of volatile cyclic polysiloxane in the cosmetic composition of the present invention, and particularly the hair cosmetic composition, can provide a comfortable feeling in use, and the molecular weight of the organopolysiloxane-polyoxyalkylene block copolymer included therein is great. As a result, superior cosmetic characteristics can be exhibited.

EXAMPLES

Hereinafter, the present invention will be described in detail based on Practical Examples and Comparative Examples. However, the present invention is not limited to these Practical Examples. Additionally, "weight average molecular weight", as used in the Practical Examples and Comparative Examples, refers to a value measured in terms of standard styrene by gel permeation chromatography.

Synthesis Example 1

A polydimethylpolysiloxane capped at both molecular terminals with hydrogen dimethylsilyl groups (viscosity: 15 mm$^2$/s, silicon-bonded hydrogen atom content: 0.13 wt %) was placed in a reaction vessel, and dehydrogenation was carried out by gradually adding a diethylhydroxyamine (DEHA100, manufactured by Adeka Corporation). Proportions of the polydimethylpolysiloxane capped at both molecular terminals with hydrogen dimethylsilyl groups and the diethylhydroxyamine in a mixture of the polydimethylpolysiloxane capped at both molecular terminals with hydrogen dimethylsilyl groups and the diethylhydroxyamine were 81.8 wt % and 18.2 wt %, respectively. After the reaction, excess DEHA was removed under 50 mmHg at 100° C. and an intermediate 1 represented by the following formula was obtained.

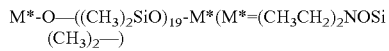

Synthesis Example 2

The polydimethylpolysiloxane capped at both molecular terminals with hydrogen dimethylsilyl groups (viscosity: 15 mm$^2$/s, silicon-bonded hydrogen atom content: 0.13 wt %), a polyethylene oxide capped at both molecular terminals with methallyl groups (manufactured by NOF Corporation, molecular weight: 600), and toluene were placed in a reaction vessel. Then a hydrosilylation catalyst (divinyltetramethyl disiloxane complex of platinum (containing 4,500 ppm of platinum as a platinum metal)) was added and an addition reaction was carried out. Proportions of the polydimethylpolysiloxane capped at both molecular terminals with hydrogen dimethylsilyl groups, the polyethylene oxide capped at both molecular terminals with methallyl groups, and the toluene in a mixture of the polydimethylpolysiloxane capped at both molecular terminals with hydrogen dimethylsilyl groups, the polyethylene oxide capped at both molecular terminals with methallyl groups, and the toluene were 38.7 wt %, 11.3 wt %, and 50 wt %, respectively. Additionally, an added amount of the hydrosilylation catalyst per 100 parts by weight of the mixture was 0.044 parts by weight. Stripping was carried out after the reaction and the silicon-bonded hydrogen atom content after the toluene was removed was 330 ppm. Here, diethylhydroxyamine (DEHA100, manufactured by Adeka Corporation) was added and dehydrogenation was carried out. An added amount of the diethylhydroxyamine per 100 parts by weight of the mixture was 2.8 parts by weight. After the reaction, excess DEHA was removed under 50 mmHg at 100° C. and an intermediate 2 represented by the following formula was obtained.

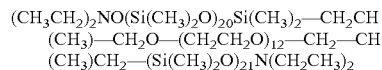

Synthesis Example 3

The polydimethylpolysiloxane capped at both molecular terminals with hydrogen dimethylsilyl groups (viscosity: 50 mm$^2$/s, silicon-bonded hydrogen atom content: 0.0435 wt %), a polyethylene oxide capped at both molecular terminals with methallyl groups (manufactured by NOF Corporation, molecular weight: 600), and toluene were placed in a reaction vessel. Then a hydrosilylation catalyst (divinyltetramethyldisiloxane complex of platinum (containing 4,500 ppm of platinum as a platinum metal)) was added and an addition reaction was carried out. Proportions of the polydimethylpolysiloxane capped at both molecular terminals with hydrogen dimethylsilyl groups, the polyethylene oxide capped at both molecular terminals with methallyl groups, and the toluene in a mixture of the polydimethylpolysiloxane capped at both molecular terminals with hydrogen dimethylsilyl groups, the polyethylene oxide capped at both molecular terminals with methallyl groups, and the toluene were 46.6 wt %, 3.4 wt %, and 50 wt %, respectively. Additionally, an added amount of the hydrosilylation catalyst per 100 parts by weight of the mixture was 0.044 parts by weight. Stripping was carried out after the reaction and the silicon-bonded hydrogen atom content after the toluene was removed was 137 ppm. Here, diethylhydroxyamine (DEHA100, manufactured by Adeka Corporation) was added and dehydrogenation was carried out. An added amount of the diethylhydroxyamine per 100 parts by weight of the mixture was 1.2 parts by weight. After the reaction, excess DEHA was removed under 50 mmHg at 100° C. and an intermediate 3 represented by the following formula was obtained.

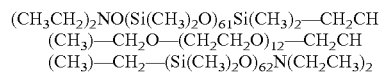

Practical Example 1

The intermediate 1 (3 wt %), the intermediate 2 (5 wt %), an amino-modified polydimethylsiloxane capped at both molecular terminals with hydroxyl groups represented by the following formula:

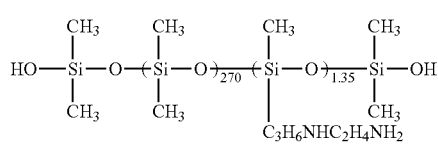

(nitrogen content: 0.2 wt %, viscosity: 1,000 mm$^2$/s; 10 wt %), a polydimethylsiloxane capped at both molecular terminals with hydroxyl groups represented by the following formula:

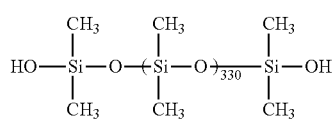

(viscosity: 2,500 mm$^2$/s; 32 wt %), and a polydimethylsiloxane capped at both molecular terminals with trimethylsilyl groups (viscosity: 20 mm$^2$/s; 50 wt %) were placed in a four-neck flask having an agitation impeller. The mixture was reacted for seven hours at 65° C. while agitating under a nitrogen atmosphere. A 50:50 mixed solution of ethanol and water (10 wt %) was added after the reaction, and agitated at room temperature for one hour. Then, the mixture was heated for two hours at 65° C. under reduced pressure. The viscosity, weight average molecular weight, and presence/absence of reactive functional groups of the obtained viscous liquid along with the contents (wt %) of octamethylcyclotetrasiloxane (hereinafter referred to as "D4"), decamethylcyclopentasiloxane (hereinafter referred to as "D5"), and dodecamethylcyclohexasiloxane (hereinafter referred to as "D6") are shown in Table 1. Note that the viscosity and the contents of D4 to D6 are shown as values measured from a mixture of the condensation reaction product and the polydimethylsiloxane having a viscosity of 20 mm$^2$/s. The weight average molecular weight is shown as a value derived from only the peak of the condensation reaction product, after measuring the mixture. The same holds true for Practical Example 2, Practical Example 3, and Practical Example 6 below.

Practical Example 2

The intermediate 1 (3 wt %), the intermediate 2 (5 wt %), the amino-modified polydimethylsiloxane capped at both molecular terminals with hydroxyl groups (nitrogen content: 0.2 wt %, viscosity: 1,000 mm$^2$/s; 10 wt %), the polydimethylsiloxane capped at both molecular terminals with hydroxyl groups (viscosity: 2,500 mm$^2$/s; 32 wt %), and the polydimethylsiloxane capped at both molecular terminals with trimethylsilyl groups (viscosity: 20 mm$^2$/s; 50 wt %) were placed in a four-neck flask having an agitation impeller. The mixture was reacted for three hours at 65° C. while agitating under a nitrogen atmosphere. A 50:50 mixed solution of ethanol and water (10 wt %) was added after the reaction, and agitated at room temperature for twelve hours. Then, the mixture was heated for two hours at 65° C. under reduced pressure. The viscosity, weight average molecular weight, and presence/absence of reactive functional groups of the obtained viscous liquid along with the contents (wt %) of D4 to D6 are shown in Table 1.

Practical Example 3

The intermediate 1 (1.75 wt %), the intermediate 3 (15 wt %), the amino-modified polydimethylsiloxane capped at both molecular terminals with hydroxyl groups (nitrogen content: 0.2 wt %, viscosity: 1,000 mm$^2$/s; 10 wt %), the polydimethylsiloxane capped at both molecular terminals with hydroxyl groups (viscosity: 2,500 mm$^2$/s; 23.25 wt %), and the polydimethylsiloxane capped at both molecular terminals with trimethylsilyl groups (viscosity: 20 mm$^2$/s; 50 wt %) were placed in a four-neck flask having an agitation impeller. The mixture was reacted for three hours at 65° C. while agitating under a nitrogen atmosphere. A 50:50 mixed solution of ethanol and water (10 wt %) was added after the reaction, and agitated at 60° C. for two hours. Then, the mixture was heated for two hours at 65° C. under reduced pressure. The viscosity, weight average molecular weight, and presence/absence of reactive functional groups of the obtained viscous liquid along with the contents (wt %) of D4 to D6 are shown in Table 1.

Practical Example 4

The intermediate 1 (2.4 wt %), the intermediate 2 (4 wt %), the amino-modified polydimethylsiloxane capped at both molecular terminals with hydroxyl groups (nitrogen content: 0.2 wt %, viscosity: 1,000 mm$^2$/s; 8 wt %), and the polydimethylsiloxane capped at both molecular terminals with hydroxyl groups (viscosity: 2,500 mm$^2$/s; 25.6 wt %) were placed in a container and agitated. Next, an emulsion having a particle size of 320 nm was obtained by adding cetyltrimethylammonium chloride (2 wt %), an ethylene oxide-propylene oxide block copolymer (EO=300 moles, PO=55 moles; 2 wt %), and water (56 wt %) to said mixture followed by emulsifying the mixture. The obtained emulsion was stored at 50° C. for two days and, thereafter, acetone, in an amount necessary to separate the polymer component, was added. The viscosity, weight average molecular weight, and presence/absence of reactive functional groups of the resulting viscous liquid separated from the emulsion along with the contents (wt %) of D4 to D6 are shown in Table 1.

Practical Example 5

The intermediate 1 (10 wt %), the intermediate 2 (6 wt %), the amino-modified polydimethylsiloxane capped at both molecular terminals with hydroxyl groups (nitrogen content: 0.2 wt %, viscosity: 1,000 mm$^2$/s; 20 wt %), and a dimethylsiloxane capped at both molecular terminals with aminoxy groups represented by the formula $(C_2H_5)_2NO[(CH_3)_2SiO]_6(CH_3)_2SiON(C_2H_5)_2$ (viscosity: 7 mm$^2$/s; 3 wt %) were placed in a container and stored at room temperature for six days. Thus, a viscous liquid having a viscosity of 2,100,000 mPa·s was obtained. The viscosity, weight average molecular weight, and presence/absence of reactive functional groups of the obtained viscous liquid along with the contents (wt %) of D4 to D6 are shown in Table 1.

Practical Example 6

The intermediate 1 (2.5 wt %), the intermediate 2 (6 wt %), the polydimethylsiloxane capped at both molecular terminals with hydroxyl groups (viscosity: 2,500 mm²/s; 41.5 wt %), and the polydimethylsiloxane capped at both molecular terminals with trimethylsilyl groups (viscosity: 20 mm²/s; 50 wt %) were placed in a four-neck flask having an agitation impeller. The mixture was reacted for three hours at 65° C. while agitating under a nitrogen atmosphere. A 50:50 mixed solution of ethanol and water (10 wt %) was added after the reaction, and agitated at 60° C. for two hours. Then, the mixture was heated for two hours at 65° C. under reduced pressure. The viscosity, weight average molecular weight, and presence/absence of reactive functional groups of the obtained viscous liquid along with the contents (wt %) of D4 to D6 are shown in Table 1.

Comparative Example 1

A polydimethylsiloxane capped at both molecular terminals with hydrogen dimethylsilyl groups (viscosity: 35 mm²/s; 38 wt %) and a polyethylene oxide-polypropylene oxide copolymer capped at both molecular terminals with methallyl groups (manufactured by NOF Corporation; molecular weight: 1,500; 32 wt %) were placed in a four-neck flask having an agitation impeller. Then, isopropyl alcohol (30 wt %) was added and 3 ppm of a divinyltetramethyl disiloxane complex of platinum (as platinum) was added at 85° C. while agitating under a nitrogen atmosphere, and the mixture was reacted for three hours. The mixture was heated under reduced pressure for two hours after the reaction and the isopropyl alcohol was removed. The viscosity, weight average molecular weight, and presence/absence of reactive functional groups of the obtained viscous liquid along with the contents (wt %) of D4 to D6 are shown in Table 2.

Comparative Example 2

The polydimethylsiloxane capped at both molecular terminals with hydrogen dimethylsilyl groups (viscosity: 35 mm²/s; 54 wt %) and the polyethylene oxide capped at both molecular terminals with methallyl groups (manufactured by NOF Corporation; molecular weight: 600; 16 wt %) were placed in a four-neck flask having an agitation impeller. Then, isopropyl alcohol (30 wt %) was added and 3 ppm of a divinyltetramethyl disiloxane complex of platinum (as platinum) was added at 85° C. while agitating under a nitrogen atmosphere, and the mixture was reacted for three hours. The mixture was heated under reduced pressure for two hours after the reaction and the isopropyl alcohol was removed. The viscosity, weight average molecular weight, and presence/absence of reactive functional groups of the obtained viscous liquid along with the contents (wt %) of D4 to D6 are shown in Table 2.

Comparative Example 3

The polydimethylsiloxane capped at both molecular terminals with hydrogen dimethylsilyl groups (viscosity: 10 mm²/s; 41 wt %) and the polyethylene oxide capped at both molecular terminals with methallyl groups (manufactured by NOF Corporation; molecular weight: 600; 31 wt %) were placed in a four-neck flask having an agitation impeller. Then, toluene (23 wt %) was added and 3 ppm of a divinyltetramethyldisiloxane complex of platinum (as platinum) was added at 85° C. while agitating under a nitrogen atmosphere, and the mixture was reacted for three hours. The mixture was heated under reduced pressure for two hours after the reaction and the toluene was removed. Then, a hydrolysate of aminoethylaminopropylmethyldimethoxysilane (4.5 wt %) and a 10% aqueous solution of potassium hydroxide (0.5 wt %) were added and reacted for five hours at 90° C. Thereafter, acetic acid was used to neutralize the potassium hydroxide and the resultant was heated under reduced pressure for two hours. The viscosity, weight average molecular weight, and presence/absence of reactive functional groups of the obtained viscous liquid along with the contents (wt %) of D4 to D6 are shown in Table 2.

Comparative Example 4

The polydimethylsiloxane capped at both molecular terminals with hydrogen dimethylsilyl groups (viscosity: 40 mm²/s; 57 wt %) and the polyethylene oxide capped at both molecular terminals with methallyl groups (manufactured by NOF Corporation; molecular weight: 600; 15 wt %) were placed in a four-neck flask having an agitation impeller. Then, toluene (23 wt %) was added and 3 ppm of a divinyltetramethyldisiloxane complex of platinum (as platinum) was added at 85° C. while agitating under a nitrogen atmosphere, and the mixture was reacted for three hours. The mixture was heated under reduced pressure for two hours after the reaction and the toluene was removed. Then, a hydrolysate of aminoethylaminopropylmethyldimethoxysilane (4.5 wt %) and a 10% aqueous solution of potassium hydroxide (0.5 wt %) were added and reacted for five hours at 90° C. Thereafter, acetic acid was used to neutralize the potassium hydroxide and the resultant was heated under reduced pressure for two hours. The viscosity, weight average molecular weight, and presence/absence of reactive functional groups of the obtained viscous liquid along with the contents (wt %) of D4 to D6 are shown in Table 2.

TABLE 1

|  | Practical Example 1 | Practical Example 2 | Practical Example 3 | Practical Example 4 | Practical Example 5 | Practical Example 6 |
| --- | --- | --- | --- | --- | --- | --- |
| Viscosity (mPa · s) | 225000 | 3700 | 28000 | 820000 | 2100000 | 3480 |
| Weight average molecular weight | 514000 | 104000 | 342000 | 185000 | 395000 | 97000 |
| Reactive functional group | Amino group | Amino group | Amino group | Amino group | Amino group | None |
| D4 | 0.05 | 0.05 | 0.05 | 0.04 | 0.03 | 0.05 |
| D5 | 0.02 | 0.02 | 0.03 | 0.04 | 0.05 | 0.01 |
| D6 | 0.04 | 0.04 | 0.06 | 0.04 | 0.05 | 0.06 |

TABLE 2

| | Comparative Example 1 | Comparative Example 2 | Comparative Example 3 | Comparative Example 4 |
|---|---|---|---|---|
| Viscosity (mPa·s) | 25900 | 3500 | 920 | 16028 |
| Weight average molecular weight | 27000 | 26000 | 12000 | 38000 |
| Reactive functional group | None | None | Amino group | Amino group |
| D4 | 0.50 | 0.50 | 0.50 | 0.03 |
| D5 | 0.50 | 1.00 | 0.50 | 1.40 |
| D6 | 0.10 | 0.96 | 0.74 | 0.96 |

The invention claimed is:

1. A manufacturing method for obtaining an organopolysiloxane-polyoxyalkylene block copolymer, said method comprising reacting: (A) a polyoxyalkylene compound represented by formula (1) below:

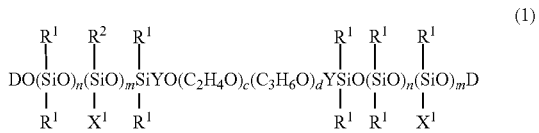

wherein:

$R^1$ are each independently a substituted or unsubstituted, straight, branched, or cyclic monovalent hydrocarbon group having from 1 to 30 carbons and that is free of unsaturated aliphatic bonds; or an alkoxy group having from 1 to 30 carbons;

$R^2$ are each independently $R^1$ or $X^1$;

$X^1$ are each independently a reactive functional group represented by —$R^3$—$Z^1$ (where $R^3$ is directly bonded or is a substituted or unsubstituted, straight or branched divalent hydrocarbon group having from 1 to 20 carbons; and $Z^1$ is an amino group-containing group or an ammonium group-containing group);

D are each independently a group selected from group represented by the formula below:

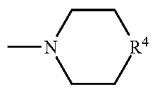

(wherein $R^4$ is an oxygen atom, a sulfur atom, or —N($R^6$)— (wherein $R^6$ is a hydrogen atom or a substituted or unsubstituted, straight, branched, or cyclic monovalent hydrocarbon group having from 1 to 30 carbons); a substituted or unsubstituted, straight or branched divalent hydrocarbon group having from 1 to 20 carbons; or a substituted or unsubstituted, straight or branched divalent hydrocarbon group comprising at least one hetero-atom and having from 1 to 20 carbons) and —N($R^5$)$_2$ (where $R^5$ is a hydrogen atom or a substituted or unsubstituted straight, branched, or cyclic monovalent hydrocarbon group having from 1 to 30 carbons);

Y are each independently a substituted or unsubstituted, straight or branched divalent organic group having from 1 to 20 carbons;

c is a number not less than 2;

d is a number not less than 0; and m are each independently a number not less than 0, n are each independently a number not less than 1, and m+n is a number in a range from 1 to 10,000; and (B) a polyorganosiloxane represented by the following formula (2):

wherein:

$R^1$, $X^1$, and $R^2$ are synonymous with those described above (however, only when E is a hydrogen atom, $R^1$ may be a hydroxyl group);

E is a hydrogen atom; and p is a number not less than 1, q is a number not less than 0, and p+q is a number in a range from 1 to 10,000;

wherein the organopolysiloxane-polyoxyalkylene block copolymer includes a unit represented by the following formula (3):

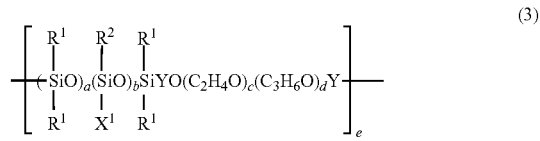

wherein $R^1$, $R^2$, $X^1$, Y, c, and d are synonymous with those described above;

a is a number not less than 1, b is a number not less than 0, and a+b is a number in a range from 1 to 10,000; and e is a number not less than 1.

2. The manufacturing method according to claim 1, wherein the $R^5$ moiety is an alkyl group having from 1 to 6 carbons.

3. The manufacturing method according to claim 1, wherein c+d is at least 4.

4. The manufacturing method according to claim 1, wherein a weight average molecular weight of a polyoxyalkylene block represented by $(C_2H_4)_c(C_3H_6)_d$ is from 200 to 15,000.

5. The manufacturing method according to claim 1, wherein a and/or e is a number not less than 2.

6. The manufacturing method according to claim 1, wherein (C) a polyorganosiloxane represented by the following formula (4) is reacted in addition to the polyoxyalkylene compound (A) and the polyorganosiloxane (B):

wherein:

$R^1$, $X^1$, $R^2$, and D are synonymous with those described above (however, only when D is a hydrogen atom, $R^1$ may be a hydroxyl group); and r is a number not less than 1, s is a number not less than 0, and r+s is a number in a range from 1 to 10,000.

7. The manufacturing method according to claim 1, wherein water or an alcohol is added during the reaction or after the reaction.

8. The manufacturing method according to claim 1, wherein an acid is added before the reaction, during the reaction, or after the reaction.

9. The manufacturing method according to claim 8, wherein the acid is an inorganic acid or an organic acid.

* * * * *